(12) United States Patent
Kahook et al.

(10) Patent No.: US 9,308,126 B2
(45) Date of Patent: Apr. 12, 2016

(54) NON-INVASIVE DEVICES AND METHODS FOR LOWERING INTRA-OCULAR PRESSURE

(71) Applicants: OcuTherix, Inc., Stillwater, MN (US); The Regents of the University of Colorado, a body corporate, Denver, CO (US)

(72) Inventors: Malik Y. Kahook, Denver, CO (US); Glenn R. Sussman, Laguna Niguel, CA (US); Robert E. Atkinson, Lake Elmo, MN (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 57 days.

(21) Appl. No.: 14/480,214

(22) Filed: Sep. 8, 2014

(65) Prior Publication Data

US 2015/0196424 A1    Jul. 16, 2015

Related U.S. Application Data

(60) Provisional application No. 62/018,770, filed on Jun. 30, 2014, provisional application No. 61/927,615, filed on Jan. 15, 2014.

(51) Int. Cl.
| | |
|---|---|
| *A61H 7/00* | (2006.01) |
| *A61F 9/00* | (2006.01) |
| *A61F 9/007* | (2006.01) |
| *A61N 7/00* | (2006.01) |

(52) U.S. Cl.
CPC .. *A61F 9/007* (2013.01); *A61N 7/00* (2013.01)

(58) Field of Classification Search
CPC ......... A61H 5/00; A61H 9/00; A61H 9/0007; A61H 9/005; A61H 2023/002; A61H 23/006; A61H 23/02; A61H 23/0254; A61H 35/02; A61H 2205/027; A61F 2007/0004; A61F 9/00; A61F 9/007; A61F 9/00736; A61F 9/00745; A61F 9/00781
See application file for complete search history.

(56) References Cited

U.S. PATENT DOCUMENTS

| | | |
|---|---|---|
| 793,004 A | 6/1905 | May |
| 1,346,724 A | 7/1920 | Roger |

(Continued)

FOREIGN PATENT DOCUMENTS

| | | |
|---|---|---|
| EP | 0 956 840 A2 | 11/1999 |
| EP | 0 956 840 B1 | 11/2007 |

(Continued)

OTHER PUBLICATIONS

European Search Report for EP Application No. 09767425.3 (6 pages).

(Continued)

*Primary Examiner* — Justine Yu
*Assistant Examiner* — Michael Tsai
(74) *Attorney, Agent, or Firm* — Michael M. McGaw; Smith & Hopen, P.A.

(57) ABSTRACT

Improvements in devices, systems and methods for non-invasively lowering intra-ocular pressure (IOP). In examples, the device applies non-invasive, focal, mechanical oscillation to the limbal region at a low amplitude and frequency, targeting the trabecular meshwork to restore outflow function and lower IOP.

29 Claims, 12 Drawing Sheets

(56) References Cited

U.S. PATENT DOCUMENTS

| | | | |
|---|---|---|---|
| 2,656,715 | A | 10/1953 | Tolman |
| 2,708,928 | A | 5/1955 | Zenatti |
| 3,308,653 | A | 3/1967 | Roth |
| 3,602,217 | A | 8/1971 | Felton et al. |
| 4,088,128 | A | 5/1978 | Mabuchi |
| 4,501,274 | A | 2/1985 | Skjaerpe |
| 4,766,904 | A | 8/1988 | Kozin et al. |
| 5,372,595 | A | 12/1994 | Gaasterland et al. |
| 5,601,548 | A * | 2/1997 | Smith et al. ............ 606/1 |
| 6,413,230 | B1 | 7/2002 | Haupt et al. |
| 6,800,061 | B1 | 10/2004 | Eklund et al. |
| 7,909,781 | B2 | 3/2011 | Schwartz |
| 2003/0028225 | A1 | 2/2003 | Chow et al. |
| 2003/0195438 | A1 | 10/2003 | Petillo |
| 2005/0033202 | A1 | 2/2005 | Chow et al. |
| 2008/0027304 | A1 | 1/2008 | Pardo et al. |
| 2008/0051681 | A1 | 2/2008 | Schwartz |
| 2008/0114427 | A1 | 5/2008 | Korb et al. |
| 2008/0200848 | A1 * | 8/2008 | Avni .................. 601/46 |
| 2011/0009779 | A1 | 1/2011 | Romano et al. |
| 2011/0087138 | A1 | 4/2011 | Kahook |
| 2013/0211395 | A1 * | 8/2013 | Schwartz ............ 606/28 |

FOREIGN PATENT DOCUMENTS

| | | |
|---|---|---|
| WO | WO 02/056805 A2 | 7/2002 |
| WO | WO 2006/129305 A2 | 12/2006 |
| WO | WO 2008/024795 | 2/2008 |

OTHER PUBLICATIONS

Gordon et al., "The Ocular Hypertension Treatment Study," Arch Ophthalmol. 2002, 120, 714-720.

Quigley et al., "The number of people with glaucoma worldwide in 2010 and 2020," Br J Ophthalmol 2006, 90, 262-267.

Wang et al., "Ultrasound Activates the TM ELAM-1/IL-1/NF-kB Response: A Potential Mechanism for Intraocular Pressure Reduction after Phacoemulsification," Invest Ophthalmol Vis Sci. May 2003, 44(5), 1977-1981.

* cited by examiner

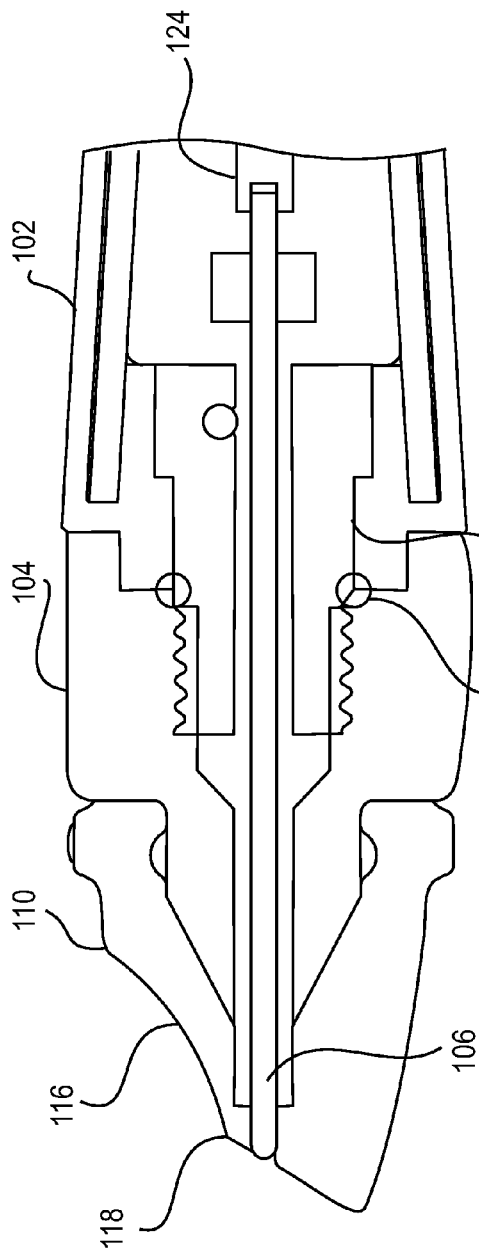
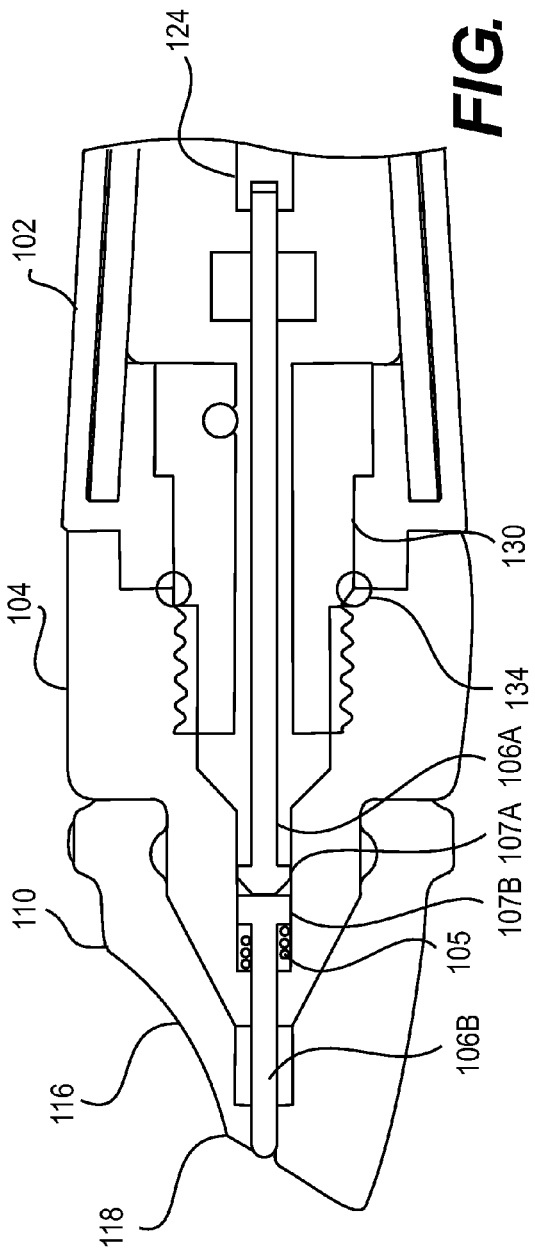

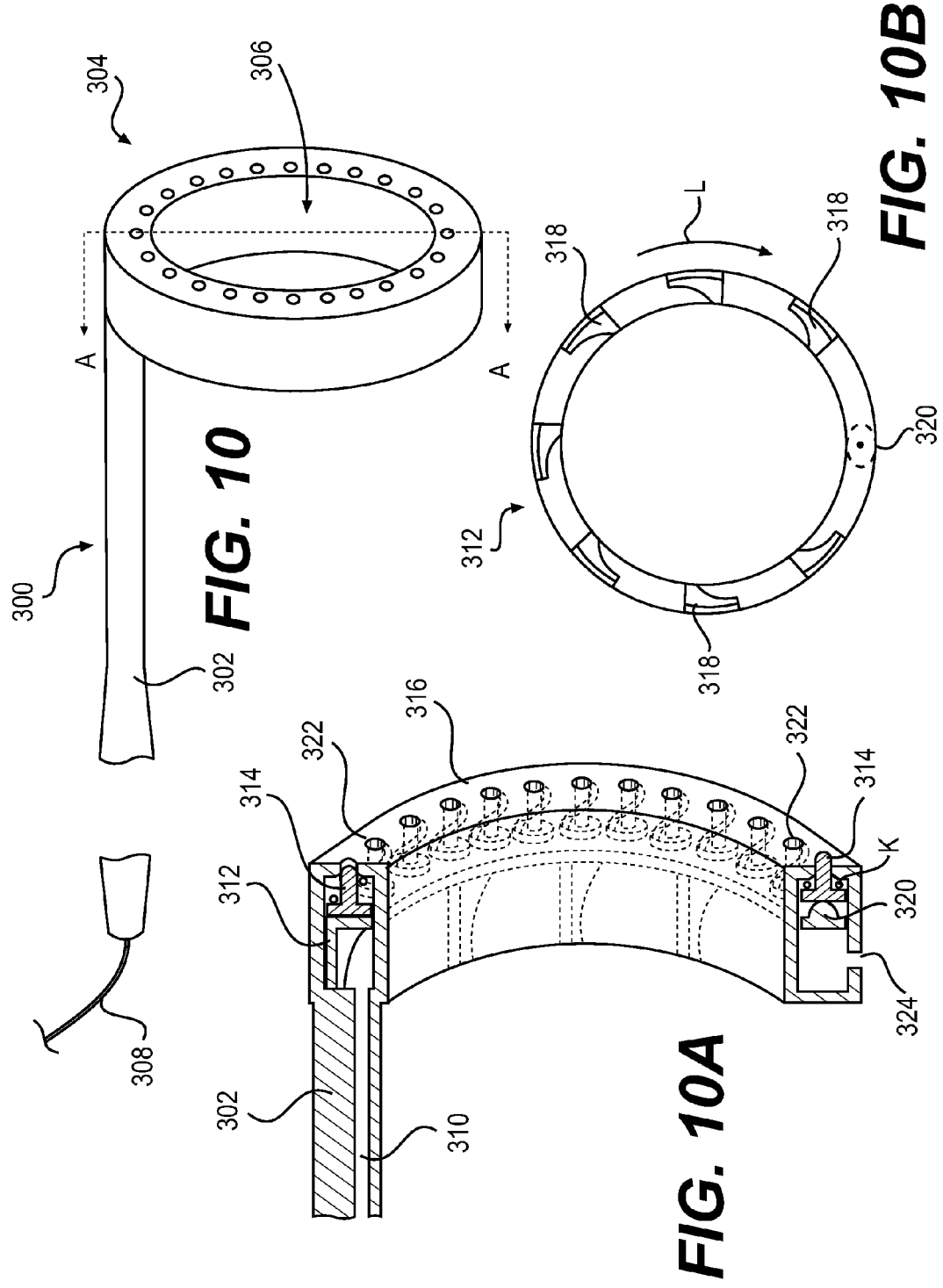

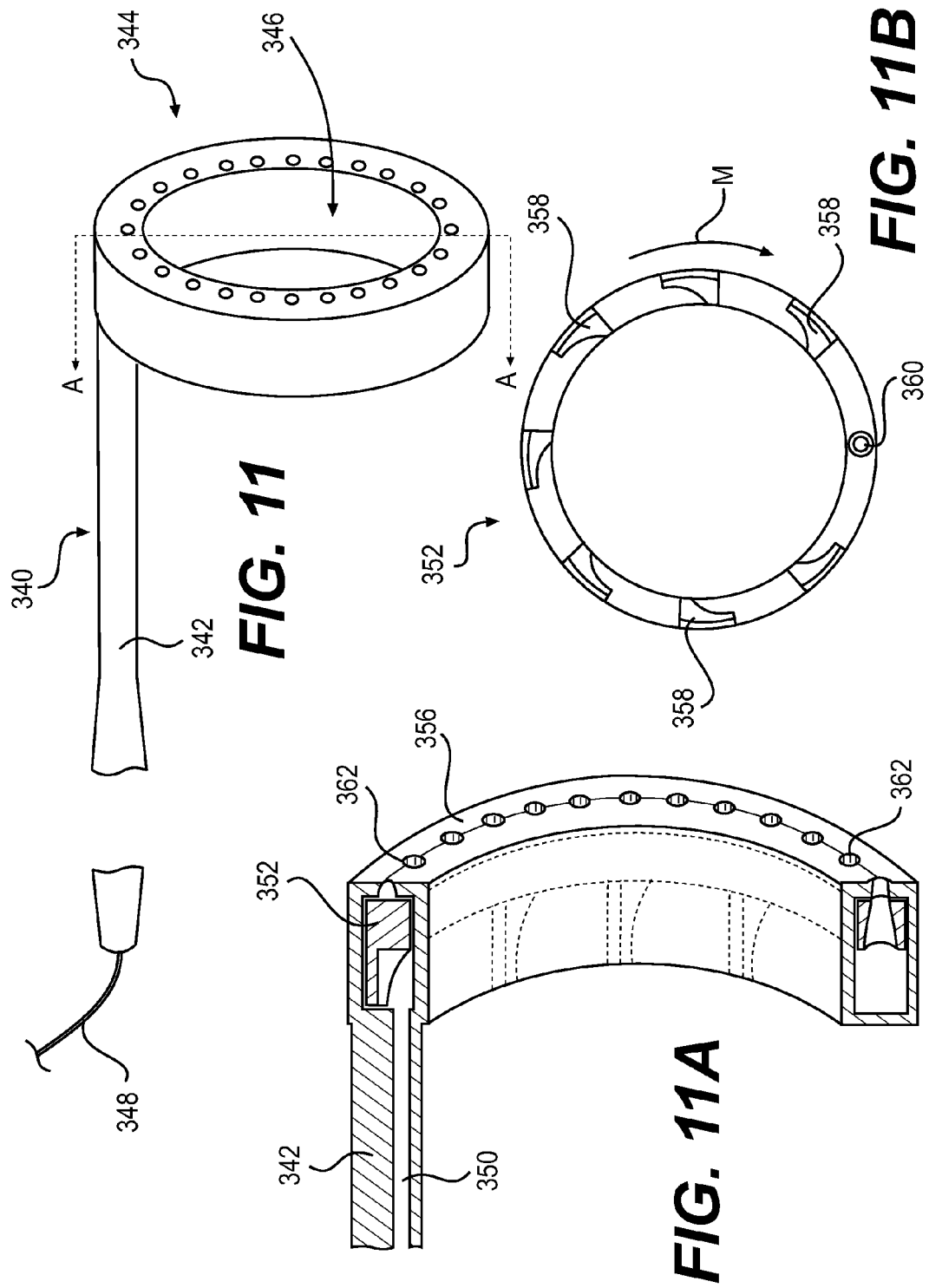

NON-INVASIVE DEVICES AND METHODS FOR LOWERING INTRA-OCULAR PRESSURE

CROSS-REFERENCE TO RELATED APPLICATIONS

This application claims the benefit of U.S. Provisional Application No. 61/927,615, filed Jan. 15, 2014, and U.S. Provisional Application No. 62/018,770, filed Jun. 30, 2014.

BACKGROUND

Glaucoma, a disease characterized by intra-ocular pressure (IOP) that is too high for the preservation of a healthy optic nerve, leads to visual field loss and blindness when left untreated. Primary open angle glaucoma (POAG), the most common form of glaucoma, effects approximately 50 million people worldwide and is the leading cause of irreversible blindness. Intra-ocular pressure is currently the only modifiable risk factor for glaucoma.

Aqueous humor drains from the eye through the conventional (trabecular meshwork) and unconventional (uveoscleral) outflow systems. In patients with ocular hypertension (OHT) or glaucoma, the conventional outflow system is dysfunctional, compromising pressure regulation and leading to elevated IOP.

Topical ophthalmic IOP-lowering medications are typically the first-line therapy for glaucoma and OHT. However, patient compliance is a significant problem. Approximately half of diagnosed glaucoma patients are on more than one daily glaucoma medication and a quarter are on maximally tolerated medical therapy. Furthermore, no medications are currently clinically available that specifically target the conventional outflow system.

Laser Trabeculoplasty (LT) is commonly a second-line treatment option for POAG utilized when medications fail. LT involves the application of thermal energy to the TM to decrease IOP, but the precise mechanism of action is unknown. Although effective in approximately half of patients up to 18 months, repeat treatments show diminished effect, probably due to its destructive nature on TM cells. Data show that LT increases cytokine release from the TM and monocyte infiltration into the eye, suggesting a mechanism of action involving thermal tissue damage and a subsequent inflammatory system activation. Such thermal injury with cell death and inflammation likely underlies the diminished responsiveness of LT upon repeated treatments.

Invasive glaucoma surgery is a third-line treatment option, but it is not broadly favored due to its complication rate and lack of sustained efficacy. The most common glaucoma surgery is trabeculectomy, which involves the creation of a hole in the sclera to bypass the conventional outflow tract and drain aqueous humor into an outer bleb. However, approximately 50% of glaucoma surgery patients experience complications (e.g., infection, leakage, and irritation) and approximately 15% are likely to require a re-operation within three years.

A relatively new group of alternative treatment options called minimally invasive glaucoma surgery (MIGS) is under investigation. While less invasive than traditional glaucoma surgery, MIGS still involves an incision, may result in permanent tissue damage, and/or has mixed efficacy results. For example, trabecular micro-bypass stenting, which involves placing a micro-stent in the TM during cataract surgery, has been demonstrated to be independently less effective than cataract surgery alone.

Ultrasonic devices are being developed to apply focused ultrasound waves to the TM or ciliary body. Focused ultrasound is destructive in soft human tissue, and causes thermal and mechanical damage to ocular tissue. In both TM and ciliary body applications, target tissue is permanently damaged, such that repeat treatments are likely to be less effective, just like repeat LT treatments are less effective. In addition, safety is a concern given the potential for collateral tissue damage to critical ocular tissues (e.g., cornea). Acceptable long term safety and efficacy has yet to shown.

Thus, there is a need for, among other things, an effective, non-invasive, atraumatic and repeatable treatment option for glaucoma and OHT patients with elevated IOP that are unable to comply with their medication regimen or on maximally tolerated medication.

SUMMARY

According to certain aspects of the present disclosure, methods of treating an eye comprise applying focal sonic oscillation to a plurality of locations on an ocular surface of the eye using a device having a treatment head, wherein each of the plurality of locations is on a limbal region of the eye, the limbal region being spaced apart from a cornea of the eye, and wherein the focal sonic oscillation applied to each of the plurality of locations includes an oscillation frequency and duration.

In some embodiments, methods of treating an eye may include one or more of the following: the plurality of locations may be disposed in a circular pattern about the cornea; the plurality of locations may include at least a first location and a second location, and a duration of the focal sonic oscillation applied to the first location may be at least partially concurrent with a duration of the focal sonic oscillation applied to the second location; the plurality of locations may include at least a first location and a second location, and the first location may be positioned 180 degrees from the second location; the plurality of locations may include at least a first location and a second location, and the first location may be spaced from the second location by less than 180 degrees; the circular pattern may be facilitated by a template to guide the treatment head; the focal oscillation may be applied by one or more pins in the treatment head; the one or more pins may be driven by one of a motor and a magnetic solenoid; the one or more pins may be driven hydraulically or pneumatically; the focal oscillation may be applied by a pulsating fluid ejected out of the treatment head; the focal oscillation may be activated when a measured pressure is within a range having a lower limit indicative of the treatment head being applied to and in contact with a surface of the eye and an upper limit corresponding to a maximum pressure threshold; the measured pressure may be measured by a sensor disposed within the treatment head; the sensor may be a load cell; each of the one or more pins may be configured to oscillate between a first position and a second position, wherein, when in the first position, the one or more pins may be withdrawn into the treatment head, and, when in the second position, a distal portion of the one or more pins may be extended out of the treatment head; the focal oscillation may be applied to the limbal region of the eye without increasing a temperature of eye tissue; the focal oscillation may be applied to the limbal region of the eye by repeatedly pressing the limbal region with a distal end of an oscillating pin; the treatment head may include a portion configured to be positioned on and in contact with a limbus of the eye; the portion may include an edge configured to complement the limbus; and the treatment head may include a distal-most surface angled relative to a longitudinal axis of the treatment head, wherein the distal-most surface may include an opening through which a distal portion of an oscillating element may extend out of the treatment head and withdraw into the treatment head.

According to certain additional aspects of the present disclosure, methods of treating an eye comprise positioning a pin of a treatment device at a first location on an ocular surface of the eye, wherein the first location is spaced from the cornea; and oscillating the pin to repeatedly apply a force to the first location, wherein the force is applied at a frequency outside of the ultrasonic range.

In some embodiments, methods of treating an eye may include one or more of the following: the treatment device may include a distal surface with an edge corresponding to a shape of the eye; the treatment device may include a nosecone configured to receive an entirety of the pin therein, and a distal surface of the nosecone may include an opening through which a distal end of portion of the pin may be configured to protrude out of the nosecone; the distal surface of the nosecone may be angled relative to an oscillating axis of the pin; the nosecone may be formed of a material that allows visualization of the pin through the nosecone; the force applied to the first location may not increase a temperature of eye tissue; the nosecone may be selectively removable from the treatment device; the pin may not pierce tissue; and the first location on the ocular surface may be at the limbus, and the force applied to the first location may be transmitted to ocular structures spaced from an exterior surface of the eye. In some embodiments, methods of treating an eye may further comprise positioning the pin at a second location on the ocular surface of the eye, wherein the second location may be spaced from the cornea; and oscillating the pin to repeatedly apply a force to the second location. In some embodiments, the first and second locations may be spaced by 180 degrees.

Additional characteristics, features, and advantages of the described embodiments will be set forth in part in the description that follows, and in part will be apparent from the description, or, may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The drawings illustrate example embodiments of the present disclosure. The drawings are not necessarily to scale, may include similar elements that are numbered the same, and may include dimensions and angles by way of example, not necessarily limitation. In the drawings:

FIG. 6A is a longitudinal sectional view of the distal assembly of the handset;

FIG. 6B is a longitudinal sectional view of an alternative (removable and disposable) distal assembly of the handset;

FIG. 10 is a perspective view of yet another alternative handset;

FIG. 10A is a sectional view taken along line A-A in FIG. 10;

FIG. 10B is a top view of the rotating ring shown in FIG. 10A;

FIG. 11 is a perspective view of a further alternative handset;

FIG. 11A is a sectional view taken along line A-A in FIG. 11; and

FIG. 11B is a top view of the rotating ring shown in FIG. 11A.

DETAILED DESCRIPTION OF THE EMBODIMENTS

Features of each and any embodiment disclosed herein may be combined with any other embodiment disclosed herein.

Figure 1:
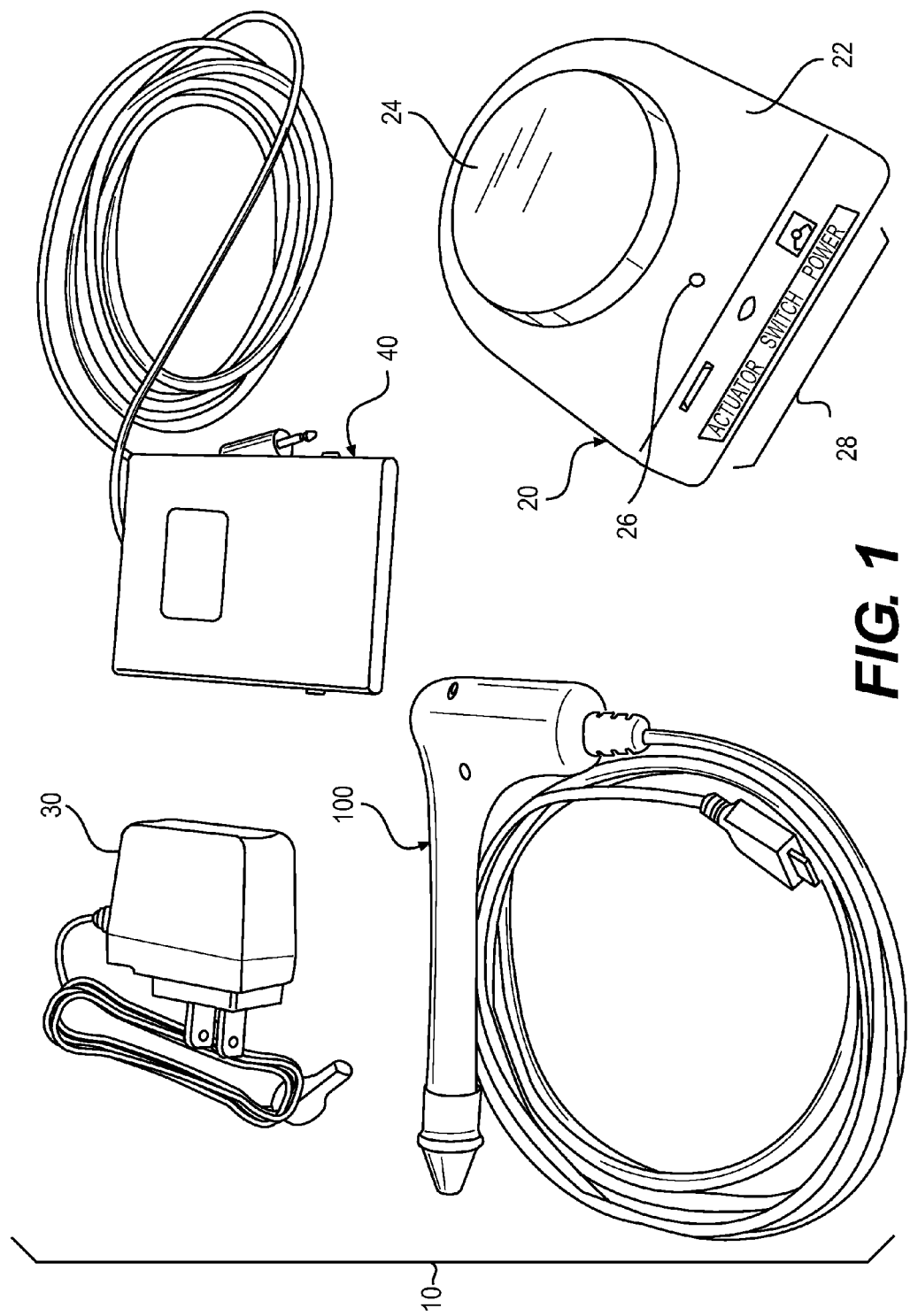
FIG. 1 is a plan view of a system according to an embodiment of the present disclosure including a control box, power source, optional foot switch and handset.

With reference to FIG. 1, a Deep Wave Trabeculoplasty (DWT) system 10 may include a control box 20, a power supply 30, an optional foot pedal switch 40, and a handset 100. As will be described in more detail hereinafter, the handset 100 may contain an electrically powered motor, a linearly oscillating probe with a distal tip, and a positioning guide. The motor may be connected to the probe via a mechanical coupler that moves the probe axially at a selected frequency (e.g., 10-500 Hz) and amplitude (e.g., 0.5-1 mm). The frequency selected for application to the patient's eye may be within a range of frequencies (e.g., sonic or sub-ultrasonic) that does not generate heat, increase the temperature of eye tissue, or otherwise damage eye tissue. The distal tip may extend beyond the positioning guide on the downward stroke, and may be set back inside the positioning guide on the upward stroke. The positioning guide may be configured to rest on the surface of the eye and conform to the limbal region such that the distal tip contacts the surface of the eye. The positioning guide thus controls the amplitude of tissue deflection while the probe tip applies mechanical oscillation proximate the limbus on the surface of the eye.

The mechanical oscillation may be transmitted to the trabecular meshwork (TM), which lies immediately posterior to the limbal region in the anterior chamber of the eye. Normal functioning TM responds to stretch to regulate the outflow of aqueous humor and control IOP. Mechanical oscillation by the DWT system 10 is believed to stretch the TM during treatment, initiating a physiological cascade to restore function of the TM and increase the outflow of aqueous humor, thereby decreasing IOP.

From the published literature, it appears that technology that causes or mimics ATP release from TM cells would be an effective therapy for glaucoma. In line with this idea, DWT therapy involves the application of mechanical vibration on the surface of the eye proximal to the limbus using the DWT system 10. The DWT system 10 causes scleral deflection (0.5-1 mm tissue displacement) on its downward stroke. Since the conventional outflow tissues reside immediately below the limbus surface, they are likely stretched upon each cycle of the distal tip. In healthy eyes, stretching of the TM by the DWT system 10 likely leads to release of ATP and activation of several signaling cascades that result in increased outflow facility and lower IOP. In glaucomatous eyes, it is likely that direct application of mechanical stress to a tissue that has become insensitive to mechanical stimuli due to disease processes and/or tissue sclerosis may activate signaling pathways that have been dormant, thus restoring outflow facility.

With continued reference to FIG. 1, the control box 20 may include a housing 22, a push-button switch 24, an indicator light 26 and several plug receptacles 28 configured to receive electrical connections from the other components 30, 40, 100. Power supply 30 (e.g., AC adapter) may provide electrical power to the control box 20 and handset 100. The foot pedal switch 40 may optionally be plugged into the control box 20, such that the foot pedal switch 40 serves as an alternative to push-button switch 24.

The housing 22 of the control box 20 may contain electronic control circuitry (not shown), which may provide power and control signals to the motor in the handset 100. The electronic control circuitry may include a timer such that depressing switch 24 (or foot pedal switch 40) activates the motor in the handset 100 for a predetermined period of time (e.g., 10 seconds) or for as long as the switch is depressed. The indicator light 26 may be illuminated when the motor in the handset 100 is activated. The control circuitry may drive the motor at a fixed or variable frequency. For example, the control circuitry may measure the load on the motor and compensate power to hold the frequency at a fixed value.

Although described as discrete components, the functionality of the control box 20 and/or power supply 30 may be incorporated into the handset 100. For example, the handset 100 may include rechargeable batteries, control circuitry, an indicator light and an activation switch. In this configuration, the handset 100 may be cordless and reside in a recharging unit when not in use.

Figure 2:
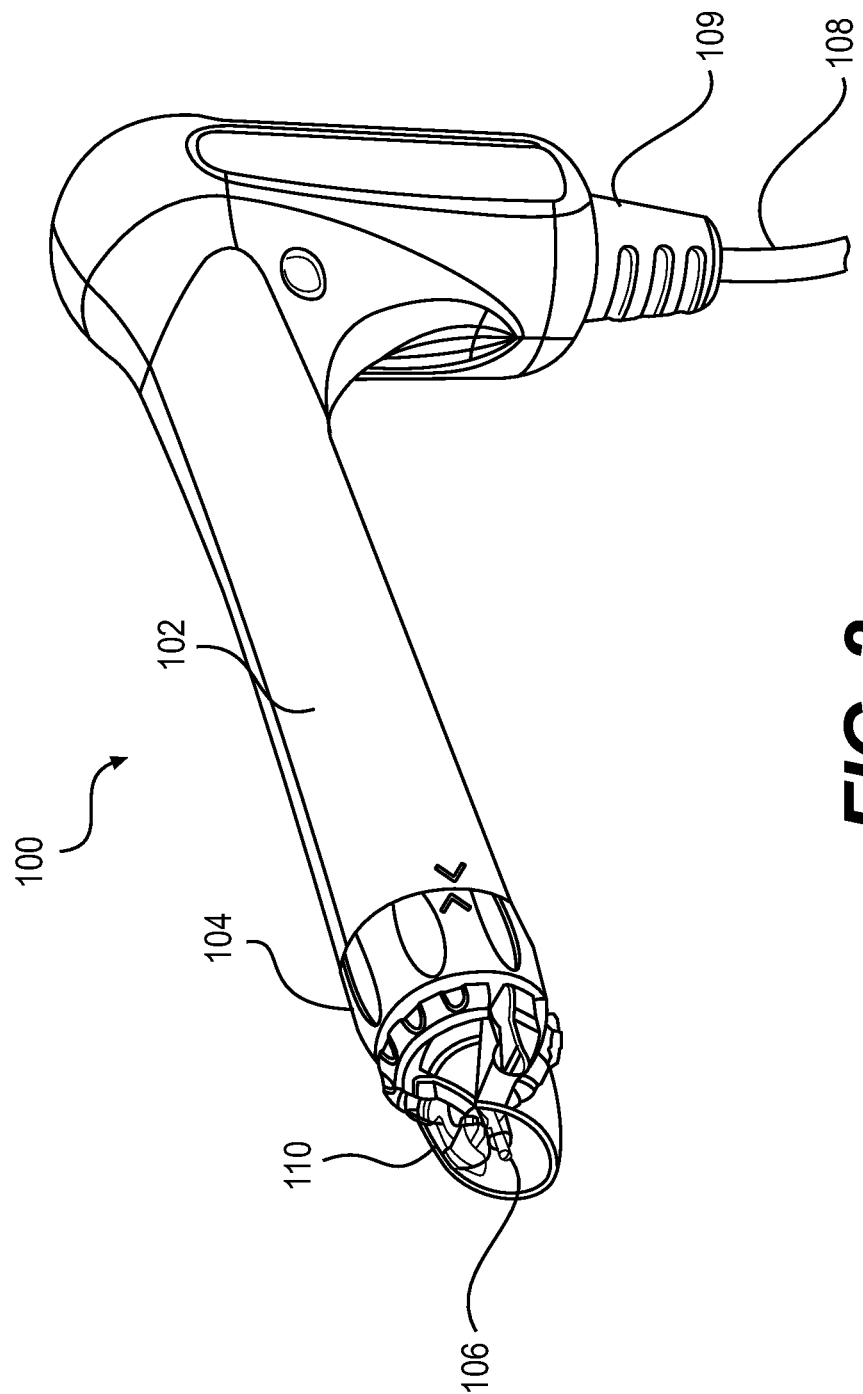
FIG. 2 is a perspective view of the handset shown in FIG. 1.

With reference to FIG. 2, the handset 100 is shown in more detail. Handset 100 may include a case 102 configured in the shape of an "L", with the long segment held in the anterior (palmar) side of the hand like a pen and the short segment resting on the posterior (dorsal) side of the hand. As will be described in more detail hereinafter, a motor may be contained in the short segment of the case 102 such that the weight of the motor is carried by the wrist and the long segment of the case 102 may be easily manipulated by the fingers for better control of the tip as it is applied to the ocular surface.

A cord 108 may be connected to the short segment of the case for connection to the control box 20. A strain relief 109 may be placed over the cord 108 and connected to the case 102 to prevent damage to the cord 108 at the junction to the case 102. The cord 108 may be electrically connected to the motor in the case as will be described in more detail hereinafter.

Figure 4A:
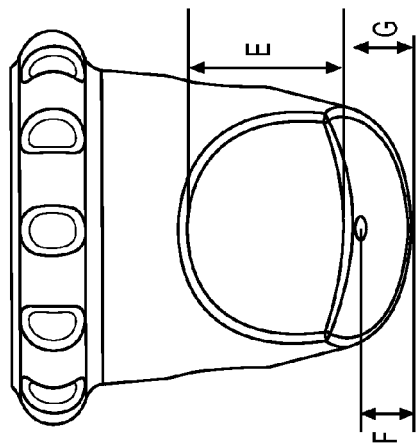
FIGS. 4A-4D are perspective, end, top and side views of a nosecone on the handset shown in FIG. 3.
Figure 4C:
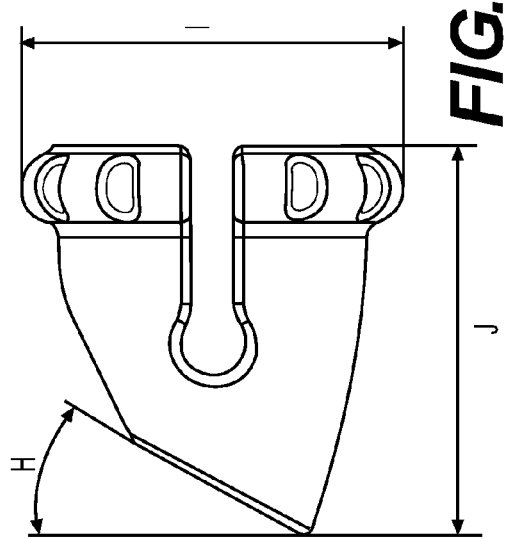
Figure 4B:
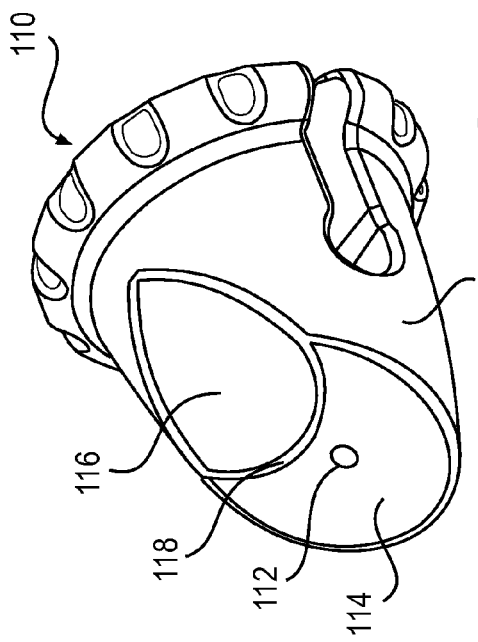
Figure 4D:
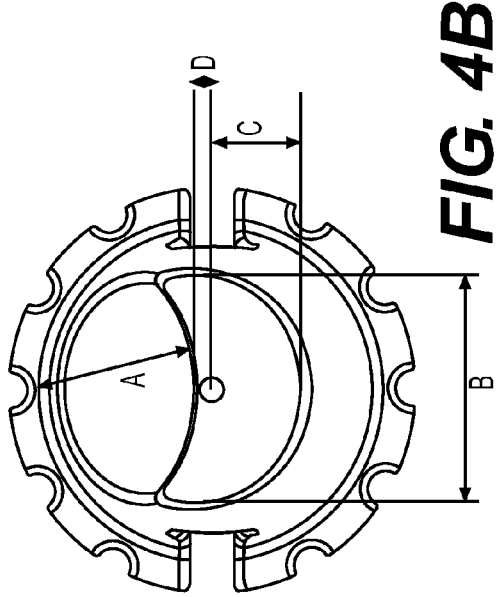

A screw-on collar 104 may be connected to the distal end of the case 102 and a snap-on nosecone 110 may be connected to the distal end of the collar 104. An oscillating pin 106 (e.g., 1.0 mm diameter) defining an atraumatic distal tip may reside in a channel in the collar 104 and nosecone 110. In some embodiments, the distal tip of pin 106 may include a semi-spherical configuration such that the tip does not pierce eye tissue when placed in contact with eye tissue. Oscillating pin 106 may oscillate between a first refracted position (see, e.g., FIG. 5) and a second extended position (see, e.g., FIG. 2). In the first retracted position, a distal end portion of oscillating pin 106 may be completely withdrawn into and received by nosecone 110. That is, in some embodiments, a distal-most tip of oscillating pin 106 may not protrude past a distal periphery of, e.g., distal surface 114 (shown in FIG. 4A, e.g.) when the pin 106 is in the first retracted position. When the pin is in the second extended position, the distal-most tip of the pin 106 may protrude beyond the distal periphery of distal surface 114. Further, the collar 104, nosecone 110 and oscillating pin 106 may be removable from the case 102 for purposes of cleaning or replacement between uses, while the remainder of the handset 100 may be reusable.

As will be described in more detail hereinafter, the nosecone 110 may include an anatomically conforming distal surface. The nosecone 110 may be formed of transparent or semi-transparent material for visualization of the pin 106 when applied to the ocular surface. The nosecone 110 may be rotatable relative to the collar 104 and case 102 to orient the distal surface thereof relative to the ocular surface without the need to rotate the entire handset 100. These features may serve to ensure proper placement of the tip of the oscillating pin 106 on the limbus and limit scleral deflection.

Figure 3:
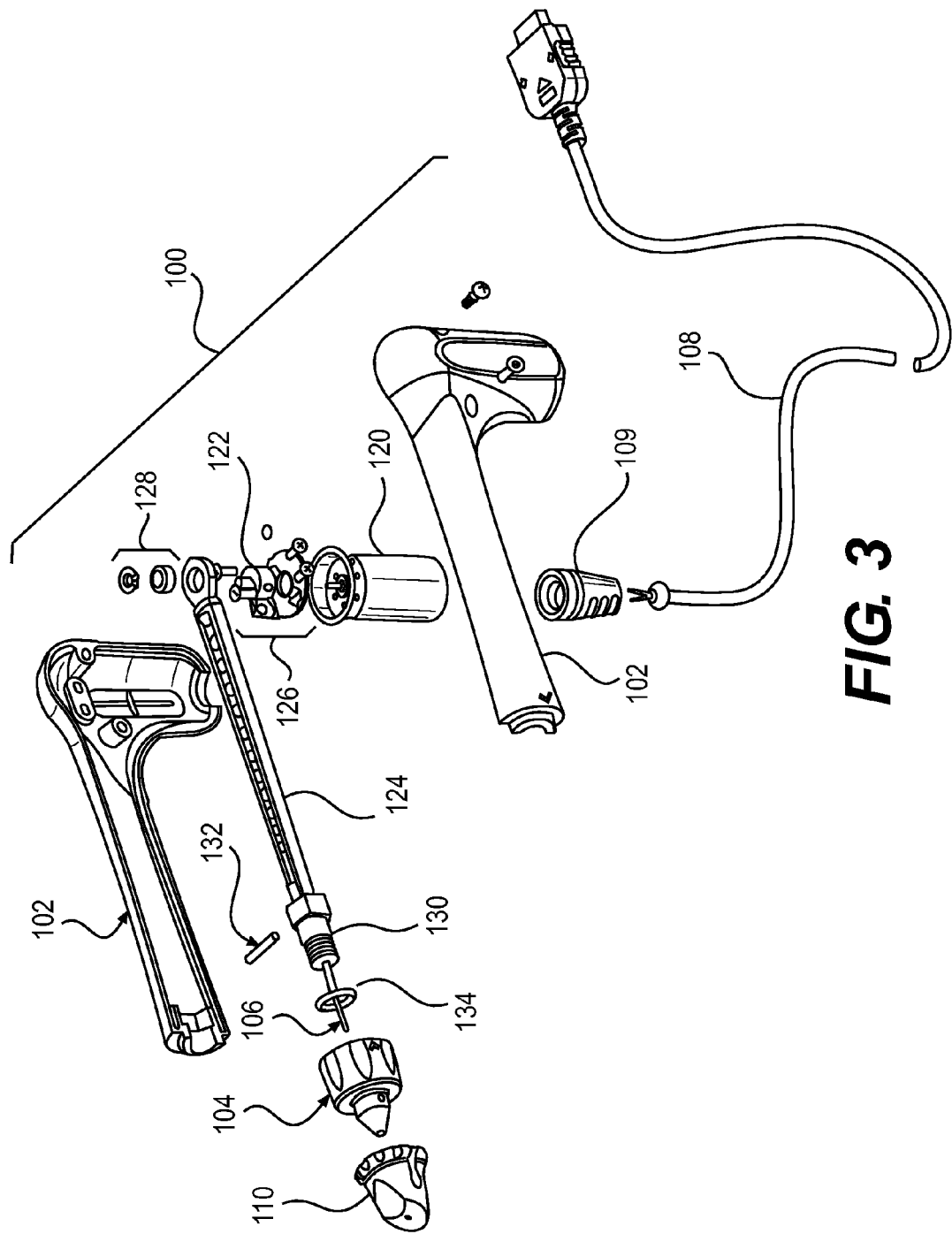
FIG. 3 is an exploded view of the handset shown in FIG. 2.

With reference to FIG. 3, the internal components of the handset 100 may be shown and described. As mentioned previously, the handset 100 includes a motor 120 that oscillates the pin 106 at a desired frequency defined by control signals from the control box 20. Motor 120 may be mechanically coupled to the pin 106 via a cam 122 and link truss 124. Whereas the oscillation frequency (e.g., sonic) of the pin 106 may be defined by the control signals sent to the motor 120 from the control box 20, the cam 122 may be used to define the oscillating amplitude (e.g., 0.5-1.0 mm) of the pin 106. The motor 120 may be mounted to the case 102 using suitable mounting hardware 126 (e.g., O-ring, L-bracket and screws). The cam 122 may be connected to the shaft of the motor 120 using conventional set screws, and the link truss 124 may be connected to the off-set shaft of the cam 122 using conventional bearing and retaining ring hardware 128. The oscillating pin 106 may be fixed to and extend from the distal end of the link truss 124. A threaded bearing 130 may be fixed to the case 102 by a fastener, such as, e.g., pin 132. The collar 104 may be screwed onto the threaded bearing 130, and an O-ring 134 may provide a fluid barrier to prevent the ingress of liquid through the channel containing the oscillating pin 106. Thus, as the motor 120 rotates cam 122, the link truss 124 moves pin 106 linearly through threaded bearing 130, collar 104 and nosecone 110.

A load cell (not shown) may be incorporated into the handset 100 and coupled to any of the nosecone 110 embodiments disclosed herein. The load cell may measure pressure applied to the nosecone 110 when the same is applied to the ocular surface. Electronics resident in the control box 20 or the handset 100 may be connected to the load cell. The electronics may activate the motor 120 automatically when the pressure is in a specified range. A lower limit of the range may indicate the nosecone 110 is being applied to the ocular surface with sufficient pressure, and an upper limit of the range may indicate too much pressure is being applied to the ocular surface.

With reference to FIGS. 4A-4D, the nosecone 110 is shown in more detail. Dimensions are provided by way of example, not necessarily limitation, and are given in millimeters. For example, with reference to FIGS. 4B-4D, dimension "A" may include a radius of about 7 mm, dimension "B" may include a distance of about 10 mm, dimension "C" may include a distance of about 4.0 mm, dimension "D" may include a distance of about 0.75 mm, dimension "E" may include a distance of about 7.1 mm, dimension "F" may include a distance of about 2.4 mm, dimension "G" may include a distance of about 3.0 mm, dimension "H" may include an angle of about 30 degrees, dimension "I" may include a distance of about 17.9 mm, and dimension "J" may include a distance of about 18.2 mm. The term "about" means to be nearly the same (or the same) as a referenced dimension. As used herein, the term "about" generally should be understood to encompass ±5% of a specific dimension.

Nosecone 110 may include a thru hole or channel 112 in which resides the oscillating pin 106. Nosecone 110 may also include a distal body portion 115 having a distal surface 114 configured to contact the limbus and sclera around the cornea. Distal surface 114 may be planar or concave with an inside contour approximating the spherical shape of the eye. Distal surface 114 may be formed at an angle (e.g., 30-60 degrees) relative to the oscillating axis of the pin 106 such that the handset 100 may be held comfortably at an angle when the nosecone 110 is applied to the ocular surface. Distal surface 114 provides a large surface area relative to pin 106 to rest on the sclera without substantial pressure, and allows the pin 106 to apply focal pressure on the limbus. Nosecone 110 may include a cutout portion 116 defining an arc 118 which may have a radius that is slightly greater than the radius of the cornea. For example, the adult cornea is typically elliptical and may have a horizontal diameter of 11.5-12.6 mm (radius of 5.75-6.3 mm) and a vertical diameter of 10.5-11.7 mm (radius of 5.25-5.85 mm). Pediatric corneas may have a diameter of 9-10 mm (radius of 4.5-5.0 mm). Thus, the radius of the arc 118 may be selected to be in the range of 4.5 mm to 7 mm, for example. Different sized nosecones 110 may be provided to accommodate the appropriate size selection of the arc 118. Cutout portion 116 and arc 118 allow the oscillating pin 106 to be positioned on the limbus without contacting the cornea. The hole 112 may have a diameter that is slightly larger than the oscillating pin diameter (e.g., 1.0 mm) and may be positioned immediately adjacent the arc 118, defining a narrow gap between the hole 112 and the arc (e.g., 0.25-1.0 mm or more preferably 0.75 mm (dimension "D" in FIG. 4B) allowing the pin 106 to be positioned immediately adjacent the cornea on the limbus. Forming the nosecone 110 of semi-transparent or transparent material allows visualization of the oscillating pin 106 and aids in precise positioning of the pin 106 on the limbus.

Figure 4E:
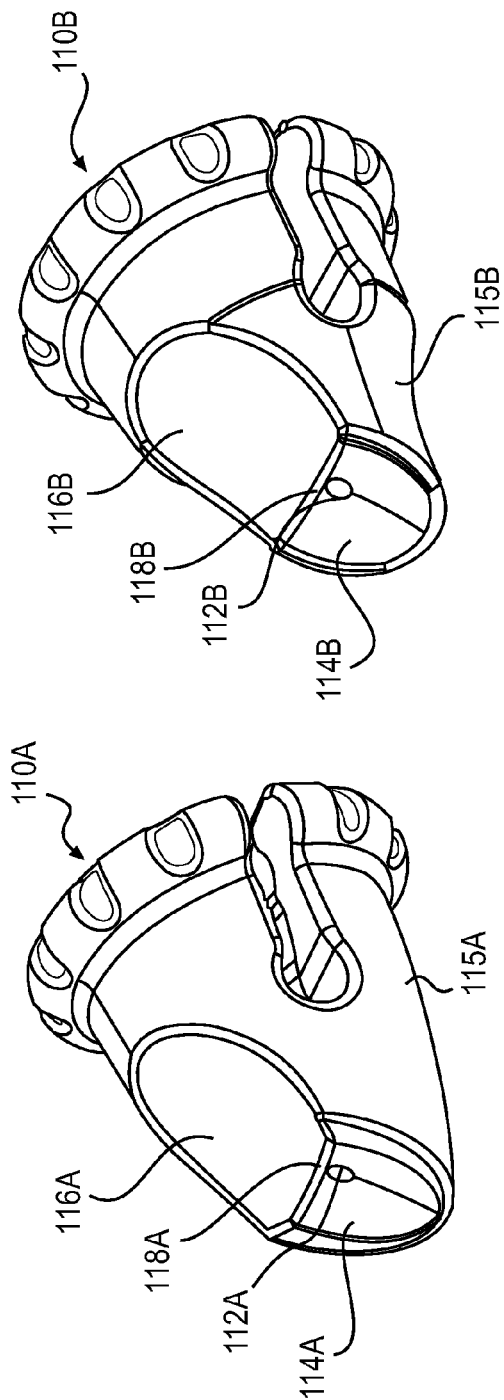
FIGS. 4E-4G are perspective views of alternative nosecone embodiments.
Figure 4F:
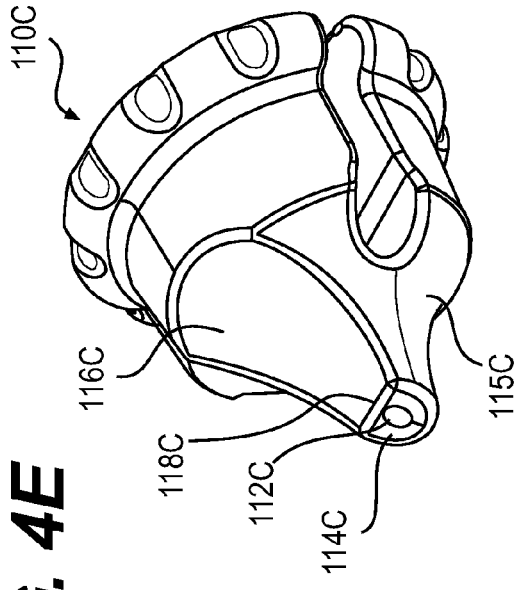
Figure 4G:
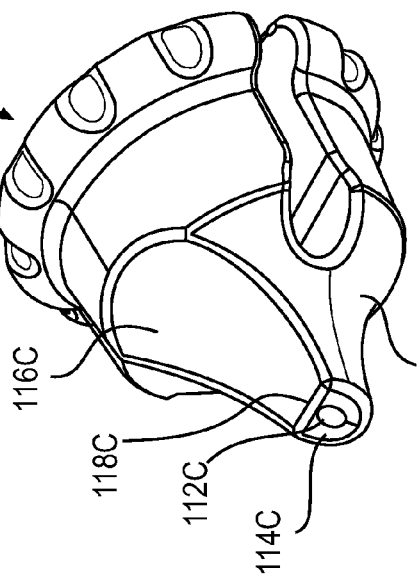

With reference to FIGS. 4E-4G, alternative nosecone embodiments are shown in perspective view. In FIG. 4E, the distal facing surface 114A of the nosecone 110A may be concave with a radius of curvature of about 12.5 mm to conform to the ocular surface where the globe of the eye has a diameter of about 25 mm (radius of about 12.5 mm). In FIG. 4F, material may be removed from the distal body portion 115B to provide for improved visualization of the pin 106 thru the transparent material of the nosecone 110B while maintaining roughly the same area of the distal facing surface 114B for contact with the ocular surface. In FIG. 4G, additional material may be removed from the distal body portion 115C to provide for improved visualization of the pin 106 thru the transparent material of the nosecone 110C while reducing the area of the distal facing surface 114C for contact with the ocular surface.

Figure 5:
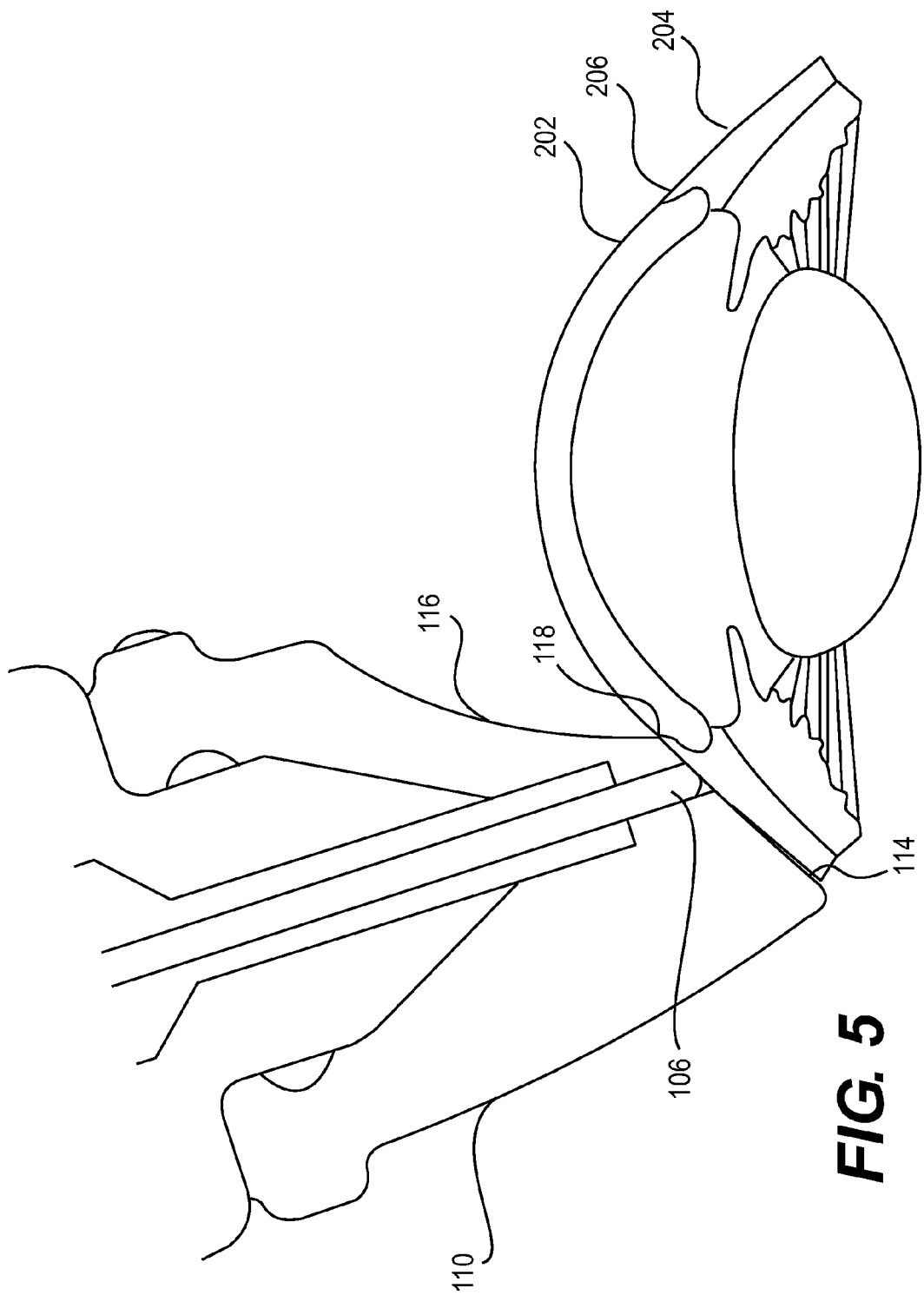
FIG. 5 is an anatomical illustration of the handset in use with the nosecone applied to the ocular surface.

With reference to FIG. 5, the position of the oscillating pin 106 relative to ocular anatomy may be better appreciated. The trabecular meshwork lies deep to the limbal region 206 defined by the transition from the cornea 202 to the sclera 204. The distal surface 114 of the nosecone 110 may be placed on the sclera 204 such that arc 118 defined by the cutout 116 is immediately adjacent the corneal edge. This position places the oscillating tip 106 on the limbus 206 to transmit focal mechanical oscillation to the trabecular meshwork.

With reference back to FIGS. 1 and 2, and continued reference to FIG. 5, clinical use of the DWT system 10 may be appreciated by the following description, given by way of example, not limitation. To prepare the DWT system for use, the tip assembly may be replaced or removed for cleaning. The nosecone 110 may be un-snapped from the collar 104 or the nosecone 110 and collar 104 assembly may be unscrewed from the threaded bearing 134. The tip assembly may be washed in soapy water and rinsed. The tip assembly (or a new one) may be replaced onto the handset 100 and all surfaces of the handset 100 may be wiped with alcohol. The handset 100 cable 108 may then be connected to the designated receptacle 28 in the control box 20. The power supply 30 may then be connected to the control box and plugged into a wall outlet. The system 10 may then be tested by depressing the button 24 on the control box 20. The tip 106 oscillates for a preset period of time (e.g., 10 sec.).

Then, with the subject supine, a lid speculum is placed on the first eye to keep the eyelids open. One drop of a suitable anesthetic, such as, e.g., proparacaine, is placed over the central cornea and repeated after 30 seconds. Lidocaine gel is then placed over the entire cornea as well as around the limbus for 360 degrees. Therapy is initiated by placing the nosecone 110 on the sclera and aligning the curved edge 118 over the limbal vessels. Gentle pressure should be used until the conjunctiva is slightly indented on either side of the nosecone 110. This pressure is preferably held constant throughout the duration of treatment. While maintaining position and pressure of the nosecone 110 as indicated, the ON button 24 on the control box 20 is then depressed, causing the tip 106 to oscillate for a specific period of time. Each quadrant of the limbus may receive 4-6 non-overlapping 10-20 second spot treatments for example, with a total of 16-36 applications around 360 degrees of the limbus. In some embodiments, therapy may be applied as deemed appropriate by a practitioner. For example, a first spot treatment may be applied at a first location and a second spot treatment may be applied at a second location that is 180 degrees (or diametrically opposed) away from the first location. In other embodiments, the second location may be adjacent (e.g., less than 180 degrees away) from the second location. Additional anesthetic (lidocaine gel) can be used to maintain patient comfort. Once the treatment is completed, the speculum is removed. The opposite eye is then treated using the identical procedure outlined above. Suitable non-inflammatory and/or pain reducing medication may be then administered to the patient. For example, in one embodiment a nonsteroidal anti-inflammatory drug such as Nevanac may be given to the subject to be used one drop four times per day in both eyes for four days.

To aid with uniform coverage, it may be desirable to mark quadrants around the limbus with a blue pen, with 4 spots 90 degrees apart from each other, for example. A ring-shaped template may be applied to the ocular surface around the treatment area for additional positioning guidance. Also, it is helpful to visualize the oscillating tip 106 thru the semi-transparent nosecone 110 to align the force vector from the tip 106 with the trabecular meshwork, which is a relatively small target (0.3 mm long). Further, it is helpful to use slight indentation of conjunctiva as indicator of correct pressure. The patient should feel vibrations throughout the treatment. Because it tip oscillation amplitude may be small (e.g., 0.5-1.0 mm), and because the oscillating tip 106 may push back, it is helpful to hold the handset 100 with steady pressure and position for the entirety of each spot treatment.

With reference to FIG. 6A, a longitudinal sectional view of the distal assembly of the handset 100 is shown. This assembly reflects the configuration shown in FIG. 3 where the oscillating pin 106 is fixed to the link truss 124 and extends through the threaded bearing 130, which in turn is fixed to the case 102 by pin 132. The collar 104 is releasably screwed onto the threaded bearing 130 with O-ring 134 providing a seal, and the nosecone 110 is releasably snapped onto the collar 104. Thus, with this arrangement, the collar 104 and nosecone 110 may be detached from the remainder of the handset, but the pin 106 remains fixed in place. This allows for replacement of the nosecone 110 and/or collar 104 and cleaning of the pin 106.

An alternative configuration is shown in FIG. 6B, which allows for replacement of all components that may come into contact with ocular tissues, including nosecone 110 and pin 106. In this embodiment, the pin 106 includes a proximal portion 106A and a distal portion 106B, with the proximal end of the proximal pin portion 106A fixed to the link truss 124 as before. The distal end of the proximal pin portion 106A includes an a head 107A that abuts but is not fixed to a corresponding head 107B on the proximal end of the distal pin portion 106B. A spring 105 may be disposed about the distal pin portion 106B to bias the distal pin portion 106B in the retracted position. With this arrangement, the proximal pin portion 106A is not fixed to the distal pin portion 106B but nevertheless provides for oscillation of the tip of the pin 106 as in prior embodiments. Specifically, the proximal pin portion 106A transfers push force to the distal pin portion 106B on the down stroke, and spring 105 retracts the distal pin portion 106B on the upstroke. This arrangement allows the distal pin portion 106B to be detached from the handset 100 by unscrewing the collar 104 such that the collar 104, pin 106B and nosecone 110 may be replaced as a single-use disposable while the remainder of the handset 100 may be reused.

Figure 7:
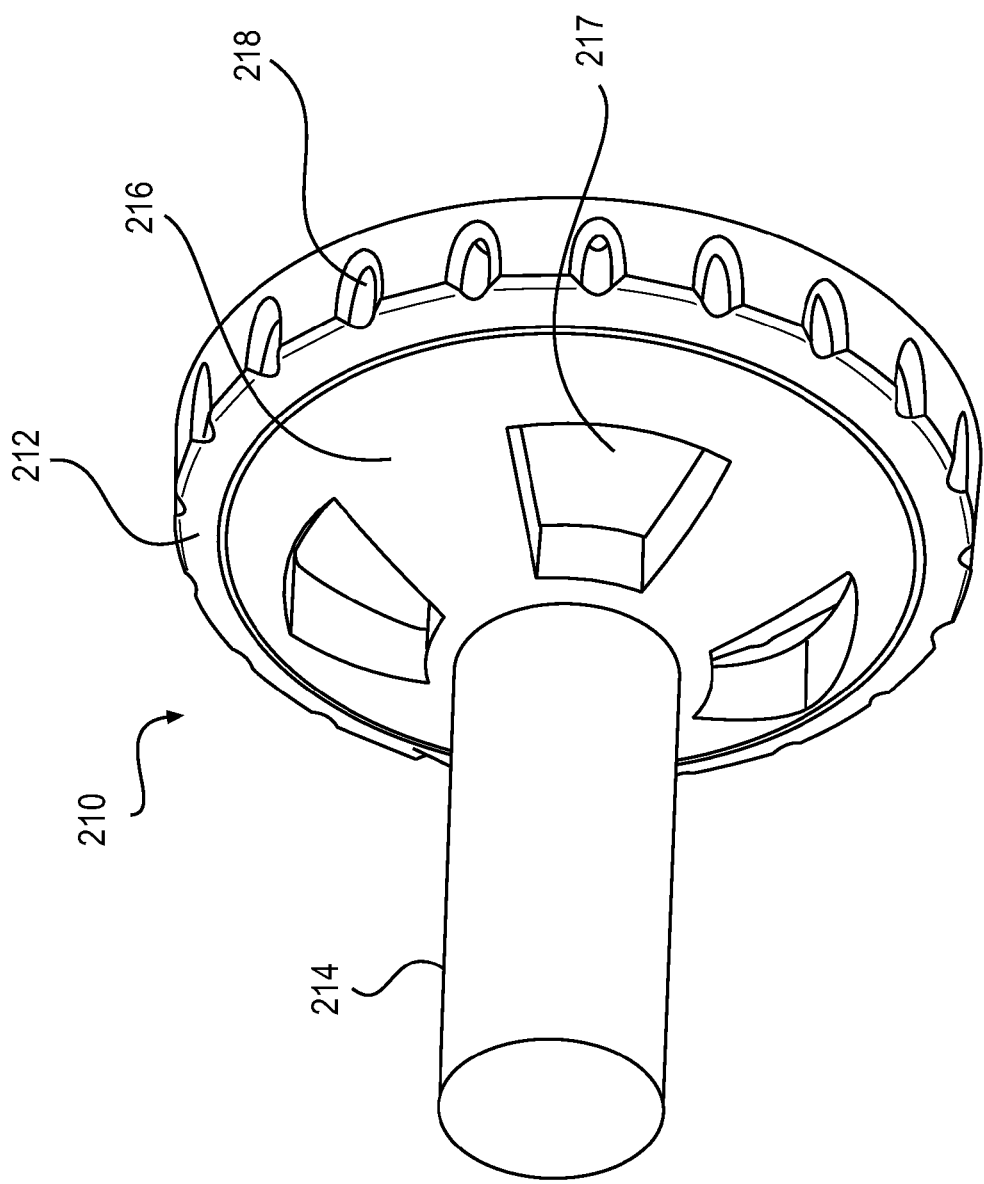
FIG. 7 is a perspective view of a template for use with the handset.

With reference to FIG. 7, a template 210 for use with the handset 100 is shown in perspective view. Template 210 may include an annular ring portion 212 connected to a handle 214 by arms 216 to define openings 217 through which the eye may be visualized. A series of holes 218 may be equally spaced around the annular ring 212. Holes 218 may be sized and configured to accommodate oscillation of the pin 106 of handset 100 while controlling the position and angle of the pin 106. The diameter of the annular ring 212 may be sized to position the holes 118 over the limbal region on the ocular surface such that the pin 106 is directed to the underlying trabecular meshwork. Because of anatomical variation, the template 210 and more specifically the diameter of the annular ring 212 along the centerline of the holes 218 may come in different sizes, ranging from about 10 mm-20 mm, for example. Additionally, the inside diameter of the annular ring 212 may be selected to avoid contact with the cornea, and may be round or oval depending on the shape of the cornea.

Template 210 is configured to be placed on the ocular surface around the limbal region and aid in positioning the pin 106 at uniformly spaced-apart spot treatments around the underlying trabecular meshwork. To accommodate the thickness of the annular ring 218 and maintain the desired excursion (e.g., 1 mm) of the pin 106, the pin 106 may be extended and/or the nosecone 110 may be replaced with a shorter-length interface to engage the template 210. Template 210 may be formed of a transparent material to allow visualization of the pin 106 engaging the ocular surface. Additionally, the tissue-contacting surface of the annular ring 212 may be formed of or include a soft atraumatic material (e.g., silicone) to reduce the likelihood of injury to the ocular surface.

Figure 8:
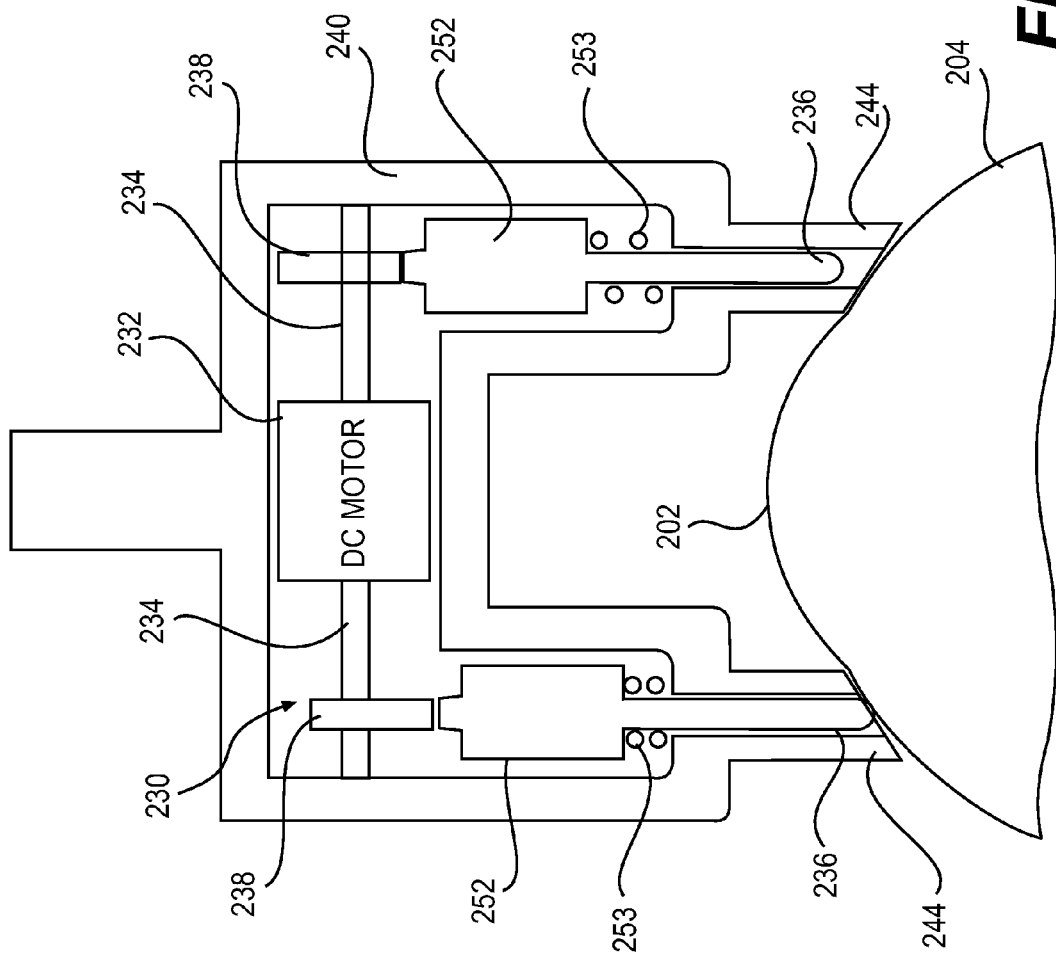
FIG. 8 is a schematic view of an alternative drive mechanism.

With reference to FIG. 8 an alternative drive mechanism 230 contained in housing 240 is shown schematically. The associated components including electrical connections and control system are not shown, but the same design principles may be applied consistent with the teachings with reference to FIG. 1 and system 10. In this embodiment, the drive mechanism 230 is used to actuate multiple pins 236 in an alternating manner. This arrangement allows for multiple spot treatments at the same time, thus reducing the procedure time. As shown, the drive mechanism 230 includes a motor 232 that rotates shaft 234 and two cams 238 offset by 180 degrees. The cams 238 displace drive cylinders 252 on the downward stroke. Springs 253 are disposed about pins 236 in the housing 240 to bias each cylinder 252 on the upward stroke. Thus, the pins 236 are driven in a linearly oscillatory fashion, causing excursion of the pins 236 from the positioning guides 244. The positioning guides 244 may be anatomically configured in a similar fashion to nosecone 110 to e.g., avoid cornea 202.

Figures 9, 9A:
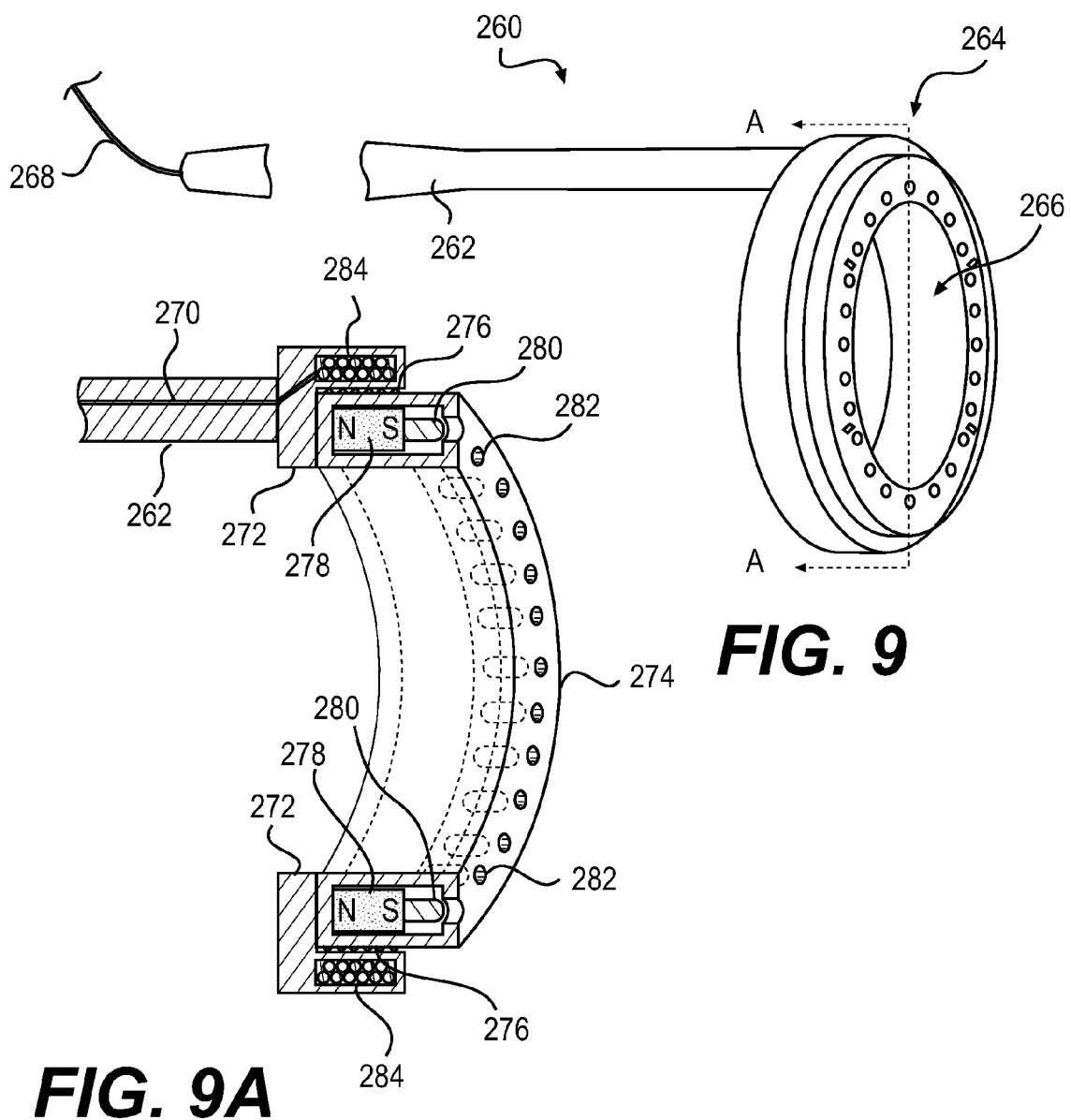
FIG. 9 is a perspective view of another alternative handset.
FIG. 9A is a sectional view taken along line A-A in FIG. 9.

With reference to FIG. 9, an alternative handset 260 in shown schematically in perspective view. Handset 260 includes a handle 262 and a magnetically driven treatment head 264 in the shape of a ring defining a through hole 266. A control cable 268 is connected to the handle 262 and is operably connected to the treatment head 264 via wires 270. As best seen in FIG. 9A, which is a sectional view taken along line A-A in FIG. 9, the treatment head 264 includes a fixed base 272 connected to the handle 262 and a detachable portion 274 connected to the fixed base 272 by threads 276. Both the fixed base 272 and the detachable portion 274 are in the shape of an annular ring, with the fixed base 272 defining an L-shaped cross-section that is configured to releasably receive the detachable portion 274 via threads 276.

With continued reference to FIG. 9A, the detachable portion 274 is hollow and contains a magnetic ring 278 with an array of pins 280 projecting therefrom. The array of pins 280 is aligned with corresponding holes 282. The magnetic ring 278 is sized and shaped relative to the hollow portion of the detachable portion 274 such that the magnetic ring 278 may be displaced longitudinally causing the pins 280 to extend out of or retract into the corresponding holes 282. Such displacement may be achieved using magnetic forces created by driver coil 284 applied to the magnetic ring 278. For example, the driver coil 284 may be powered by an alternating electrical signal to drive the magnetic ring 278 in alternating posterior and anterior directions, causing the pins to oscillate in a longitudinal (anterior-posterior) direction at a frequency corresponding to the frequency of the alternating electrical signal. With the treatment head 264 placed on the ocular surface, the through hole 266 centered around the cornea such that cornea is not contacted, and the holes 282 aligned with the limbal region, the pins 282 may apply mechanical oscillating forces to the underlying trabecular meshwork simultaneously. The size, number and arrangement of the pin array 280 and corresponding holes 282 may vary. In addition, the magnetic ring 278 may be a continuous ring with uniform polarity such that all pins 280 are advanced and retracted in unison, or the magnetic ring 278 may be divided into discrete arc sections with alternating polarity such that pins 280 corresponding to adjacent arc sections are alternately advanced and retracted.

With reference to FIG. 10, another alternative handset 300 in shown schematically in perspective view. Handset 300 includes a handle 302 and a fluid driven treatment head 304 in the shape of a ring defining a through hole 306. A fluid line 308 is connected to the handle 302 and is operably connected to the treatment head 304 via lumen 310. As best seen in FIGS. 10A and 10B, the treatment head 304 includes a rotating ring 312 and an array of spring loaded pins 314 disposed in a hollow ring housing 316. The rotating ring 312 includes spaced-apart turbine blades 318 and one or more spaced-apart cams 320 that engage the base of the pins 314. The hollow ring housing 316 includes a series of holes 322 aligned with and corresponding to the pins 314.

With continued reference to FIGS. 10A and 10B, the rotating ring 312 may be driven by pressurized fluid (liquid or gas) via pressure line 308 and lumen 310 causing rotation of the ring 312 as the fluid engages the turbine blades 318 and eventually exits exhaust port 324. As the ring 312 rotates, the cam (or cams) 320 sequentially engages the base of each spring-loaded pin 314, causing displacement of the pin 314 such that it extends through the corresponding hole 322 of the housing. As ring 312 continues to rotate and the cam 320 passes each pin 314, the associated spring causes the pin 314 to retract back into the housing 316. With this arrangement, the pins 314 sequentially oscillate longitudinal (anterior-posterior) direction at a frequency corresponding to the pressure-controlled rotational velocity or ring 312 and the number of cams 320. With the treatment head 304 placed on the ocular surface, the through hole 306 centered around the cornea and without contacting the cornea, and the holes 322 aligned with the limbal region, the pins 314 may apply mechanical oscillating forces to the underlying trabecular meshwork sequentially around the circumference. The size, number and arrangement of the pin array 314 and corresponding holes 322 may vary. In addition, number and spacing of the cams 320 may vary to provide the desired number, timing and circumferential position of pins 314 actuated.

With reference to FIG. 11, yet another alternative handset 340 in shown schematically in perspective view. Handset 340 includes a handle 342 and a fluid driven treatment head 344 in the shape of a ring defining a through hole 346. A fluid line 348 is connected to the handle 342 and is operably connected to the treatment head 344 via lumen 350. As best seen in FIGS. 11A and 11B, the treatment head 344 includes a rotating ring 352 including spaced-apart turbine blades 358 and one or more spaced-apart exhaust ports 360. The rotating ring 352 is disposed in a hollow ring housing 356 that includes a series of holes 362.

With continued reference to FIGS. 11A and 11B, the rotating ring 352 may be driven by pressurized fluid (liquid or gas) via pressure line 348 and lumen 350 causing rotation of the ring 352 as the fluid engages the turbine blades 358 and eventually exits exhaust port 360 when aligned with one of the holes 362. As the ring 352 rotates, the exhaust port (or ports) 360 sequentially aligns with each hole 362 in the housing 356. The fluid then exits the hole 362, acting as a fluid equivalent of the pins described in other embodiments. With this arrangement, fluid pulses sequentially exit in a longitudinal (posterior) direction at a frequency corresponding to the pressure-controlled rotational velocity or ring 352 and the number of exhaust ports 360. With the treatment head 344 placed on the ocular surface, the through hole 346 centered around the cornea such that treatment head 344 does not contact the cornea, and the holes 362 aligned with the limbal region, the exhaust fluid may apply mechanical oscillating forces to the underlying trabecular meshwork sequentially around the circumference. The size, number and arrangement of the holes 362 may vary. In addition, number and spacing of the exhaust ports 360 may vary to provide the desired number, timing and circumferential position of fluid pulses.

In any of the foregoing embodiments, irrigation may be supplied to the treatment head to lubricate the spot treatment area. Suitable liquids include balanced salt solutions and other topical irrigation fluids. In addition or in the alternative, the treatment head may include a seal ring (e.g. silicone) about its distal-facing perimeter to provide a cushion and/or seal against the ocular surface. In addition or in the alternative, the treatment head may incorporate a vacuum to stabilize the device against the ocular surface.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A method of treating an eye, the method comprising: applying focal sonic oscillation to a plurality of locations on an ocular surface of the eye using a device having a treatment head, wherein each of the plurality of locations is on a limbal region of the eye, the limbal region being spaced apart from a cornea of the eye, and wherein the focal sonic oscillation applied to each of the plurality of locations includes an oscillation frequency and a duration, wherein the focal oscillation is activated when a measured pressure is within a range having a lower limit indicative of the treatment head being applied to and in contact with a surface of the eye and an upper limit corresponding to a maximum pressure threshold.

2. The method of claim 1, wherein the plurality of locations is disposed in a circular pattern about the cornea.

3. The method of claim 1, wherein the plurality of locations includes at least a first location and a second location, and wherein a duration of the focal sonic oscillation applied to the first location is at least partially concurrent with a duration of the focal sonic oscillation applied to the second location.

4. The method of claim 2, wherein the plurality of locations includes at least a first location and a second location, and wherein the first location is positioned 180 degrees from the second location.

5. The method of claim 2, wherein the plurality of locations includes at least a first location and a second location, and wherein the first location is spaced from the second location by less than 180 degrees.

6. The method of claim 2, wherein the circular pattern is facilitated by a template to guide the treatment head.

7. The method of claim 1, wherein the focal oscillation is applied by one or more pins in the treatment head.

8. The method of claim 7, wherein the one or more pins are driven by one of a motor and a magnetic solenoid.

9. The method of claim 7, wherein the one or more pins are driven hydraulically or pneumatically.

10. The method of claim 1, wherein the focal oscillation is applied by a pulsating fluid ejected out of the treatment head.

11. The method of claim 1, wherein the measured pressure is measured by a sensor disposed within the treatment head.

12. The method of claim 11, wherein the sensor is a load cell.

13. The method of claim 7, wherein each of the one or more pins is configured to oscillate between a first position and a second position, wherein, when in the first position, the one or more pins are withdrawn into the treatment head, and, when in the second position, a distal portion of the one or more pins is extended out of the treatment head.

14. The method of claim 1, wherein the focal oscillation is applied to the limbal region of the eye without increasing a temperature of eye tissue.

15. The method of claim 1, wherein the focal oscillation is applied to the limbal region of the eye by repeatedly pressing the limbal region with a distal end of an oscillating pin.

16. The method of claim 1, wherein the treatment head includes a portion configured to be positioned on and in contact with a limbus of the eye.

17. The method of claim 16, wherein the portion includes an edge configured to complement the limbus.

18. The method of claim 1, wherein the treatment head includes a distalmost surface angled relative to a longitudinal axis of the treatment head, wherein the distalmost surface includes an opening through which a distal portion of an oscillating element may extend out of the treatment head and withdrawn into the treatment head.

19. A method of treating an eye, the method comprising:
positioning a pin of a treatment device at a first location on an ocular surface of the eye, wherein the first location is spaced from the cornea; and
oscillating the pin to repeatedly apply a force to the first location, wherein the force is applied at a frequency outside of the ultrasonic range, wherein the force from the oscillating of the pin is activated when a measured pressure is within a range having a lower limit indicative of the pin being applied to and in contact with to the ocular surface of the eye and an upper limit corresponding to a maximum pressure threshold.

20. The method of claim 19, wherein the treatment device includes a distal surface with an edge corresponding to a shape of the eye.

21. The method of claim 19, wherein the treatment device includes a nosecone configured to receive an entirety of the pin therein, and a distal surface of the nosecone includes an opening through which a distal end of portion of the pin is configured to protrude out of the nosecone.

22. The method of claim 21, wherein the distal surface of the nosecone is angled relative to an oscillating axis of the pin.

23. The method of claim 20, wherein the nosecone is formed of a material that allows visualization of the pin through the nosecone.

24. The method of claim 19, wherein the force applied to the first location does not increase a temperature of eye tissue.

25. The method of claim 21, wherein the nosecone is selectively removable from the treatment device.

26. The method of claim 19, wherein the pin does not pierce tissue.

27. The method of claim 19, wherein the first location on the ocular surface is at the limbus, and the force applied to the first location is transmitted to ocular structures spaced from an exterior surface of the eye.

28. The method of claim 19, further comprising:
positioning the pin at a second location on the ocular surface of the eye, wherein the second location is spaced from the cornea; and
oscillating the pin to repeatedly apply a force to the second location.

29. The method of claim 28, wherein the first and second locations are spaced by 180 degrees.

* * * * *